(12) United States Patent
Cohen et al.

(10) Patent No.: US 7,572,764 B2
(45) Date of Patent: Aug. 11, 2009

(54) USES OF CHEMICALLY-MODIFIED CHOLINESTERASES FOR DETOXIFICATION OF ORGANOPHOSPORUS COMPOUNDS

(75) Inventors: Ofer Cohen, Moshav Netaim (IL); Chanoch Kronman, Rehovot (IL); Theodor Chitlaru, Rehovot (IL); Baruch Velan, Tel-Aviv (IL); Avigdor Shafferman, Nes Ziona (IL)

(73) Assignee: State of Israel Prime Minister's Office Israel Institute for Biological Research, Neg Ziona (IL)

( * ) Notice: Subject to any disclaimer, the term of this patent is extended or adjusted under 35 U.S.C. 154(b) by 353 days.

(21) Appl. No.: 10/476,338

(22) PCT Filed: Apr. 25, 2002

(86) PCT No.: PCT/IL02/00329

§ 371 (c)(1), (2), (4) Date: Feb. 4, 2004

(87) PCT Pub. No.: WO02/087624

PCT Pub. Date: Nov. 7, 2002

(65) Prior Publication Data

US 2004/0147002 A1 Jul. 29, 2004

(30) Foreign Application Priority Data

Apr. 30, 2001 (IL) .................................. 142875

(51) Int. Cl.
*A61K 31/70* (2006.01)
*A61K 38/00* (2006.01)
(52) U.S. Cl. ............................................ 514/2; 514/23
(58) Field of Classification Search ............ 514/2, 514/23
See application file for complete search history.

(56) References Cited

U.S. PATENT DOCUMENTS

| | | | | |
|---|---|---|---|---|
| 4,179,337 A | * | 12/1979 | Davis et al. | .................. 435/181 |
| 5,695,750 A | * | 12/1997 | Doctor et al. | .............. 424/94.1 |
| 6,214,966 B1 | | 4/2001 | Milton | |
| 2002/0119489 A1 | * | 8/2002 | Lockridge et al. | ............ 435/7.1 |

FOREIGN PATENT DOCUMENTS

| | | |
|---|---|---|
| EP | 442724 | 8/1991 |
| WO | WO 95/00162 | 4/1995 |
| WO | WO 00/64957 | 11/2000 |
| WO | WO 00/73427 | 12/2000 |

OTHER PUBLICATIONS

Andrianov: Polymer hydrogel for . . . solution: and SU 1,705,318 (Univ Moscovski) Jan. 15, 1992; XP002207571, Abstract only.
Andrianov: Covalent Immobilizaiton of . . . hydrogels; vol. 318, No. 5, 1991, pp. 1250-1253; XP002207572, Abstract only.
Guerra: PEGylation prevents the . . . factor; Pharmaceutical Research, vol. 15, No. 12, Dec. 1998, pp. 1822-1827, XP001088977.
LeJeune: Fighting Nerve Agent Chemical Weapons with Enzyme Technoloy; Annals of New York Academy of Sciences, vol. 864, pp. 153-170, 1998, XP00938254.

* cited by examiner

*Primary Examiner*—Ruth A Davis
(74) *Attorney, Agent, or Firm*—Roach Brown McCarthy & Gruber, P.C.; Kevin D. McCarthy

(57) ABSTRACT

A circulatory long-lived cholinesterase (ChE) protein, such as acetylcholinesterase (AChE) or butyrylcholinesterase (BChE), which is a ChE protein modified with a non-antigenic polymer. The ChE may be AChE, such as native AChE of mammalian origin or of non-mammalian origin, or recombinant AChE. The recombinant AChE may be mutated at one or more amino-acid residues. The BChE may be native BChE of mammalian origin or of non-mammalian origin.

8 Claims, 11 Drawing Sheets

USES OF CHEMICALLY-MODIFIED CHOLINESTERASES FOR DETOXIFICATION OF ORGANOPHOSPORUS COMPOUNDS

FIELD OF THE INVENTION

The present invention relates to the chemical modification of cholinesterases (ChEs) by polyethylene glycol (PEG), to proteins of improved stability and circulatory half-life obtained thereby, to pharmaceutical comprising them, and their uses.

BACKGROUND OF THE INVENTION

Conjugating biologically active proteins to polymers has been shown to improve the circulating life of the administered protein and to reduce its antigenicity and immunogenicity. For example, U.S. Pat. No. 4,179,337 discloses the use of PEG or polypropylene glycol coupled to proteins to provide a physiologically active non-immunogenic water soluble polypeptide composition. Conjugates are formed by reacting a biologically active material with a several fold molar excess of a polymer which has been modified to contain a terminal linking group.

A variety of means have been used to attach polyethylene glycol molecules to the protein. For example, U.S. Pat. No. 5,932,464 and U.S. Pat. No. 5,990,237 disclose methods for coupling polyethylene glycol to a biomaterial. Generally, polyethylene glycol molecules are connected to a protein via a reactive group found thereon. Amino groups, such as those on lysine residues or at the N-terminus, as well as thiol groups on cysteine, or other reactive groups on protein surface, are convenient for such attachment. For many biologically active materials, however, the conjugation process is accompanied by several complications. Firstly, it is not always specific with regard to attachment sites. Secondly, loss of biological activity is often caused by the conjugation reaction. For example, if too much of the activated polymer is attached to the target protein or polypeptide, biological activity can be severely reduced or lost. Furthermore, if the wrong linker joining the polymer to the protein is used, or if an insufficient amount of polymer is attached to the target, the therapeutic value of the resultant conjugate is limited. Often, such conjugates do not demonstrate enough of an increase in the circulating life to compensate for the loss in bioactivity. Problems can also result when a therapeutic moiety's active site (i.e. where groups associated with bioactivity are located) becomes sterically blocked as a result of the polymer attachment. Accordingly, the outcome of a protein conjugation process is unpredictable in nature.

Cholinesterases are important proteins. Acetylcholinesterase (AChE, EC 3.1.1.7) plays a pivotal role in the cholinergic system where it functions in the rapid termination of nerve impulse transmission. The function of the related enzyme butyrylcholinesterase (BChE, EC 3.1.1.8) is yet unknown, nor is its specific natural substrate known, but it is capable of hydrolysing acetylcholine. It has been suggested that BChE acts as an endogenous scavenging enzyme important for the detoxification of natural poisons [Massoulie, J., et al., (1993) Prog. Brain Res. 98, 139-146]. The high reactivity of these enzymes toward organophosphorus (OP) compounds, makes exogenous cholinesterase an effective therapeutic agent in the prophylaxis and treatment of OP-poisoning. Indeed the successful exploitation of the scavenging potential of various forms of cholinesterases which include fetal bovine AChE [Maxwell, D. M., et al., (1992) Toxicol. Appl. Pharmacol. 115, 44-49], human BChE [Raveh, L., et al., (1993) Biochem. Pharmacol. 45, 37-41], equine BChE [Broomfield, C. A., et al., (1991) J. Pharmacol. Exp. Ther. 259, 683-698] has been demonstrated in rodents [Raveh, L., et al., ibid] and in non-human primates [Broomfield, C A, et al., ibid; Maxwell D M et al., ibid] and even for treatment of humans exposed to organophosphate pesticides [Cascio, C., et al., (1988) Minerva Anestesiol. 54, 337-338].

The use of ChE as a biological scavenger requires sources for large quantities of purified enzyme and depends on the retention of the enzyme in the circulation for sufficiently long periods of time. Production of AChE in various expression systems is known. However, the successful application of recombinant ChE as a bioscavenging agent of therapeutic value requires its retention within the circulation for appreciable periods of time. Examination of the pharmacokinetic profile of various recombinant AChEs demonstrates that these are eliminated from the circulation rapidly, displaying mean residence time values (MRT) of 5-100 minutes [Kronman, C., et al., (1992) Gene 121, 295-304; Chitlaru, T., et al., (1998) Biochem. J. 336, 647-658], and therefore do not meet the requirements for OP bioscavenging in their non-modified state.

It would therefore be desirable to be able to provide ChEs that exhibit improved retention within the circulation, which could be used as therapeutic bioscavenging agents. It has now been surprisingly found, and this is an object of the present invention, that it is possible to provide such improved modified ChEs, by a modification made using polyethylene glycol groups attached to the lysine moieties located on the ChEs.

It is thus an object of the invention to provide such modified ChEs which exhibit excellent and unprecedented circulatory longevity.

It is another object of the invention to provide a beneficial extension of circulatory residence by polyethylene glycol appendage, which overrides the various deleterious factors which contribute to the rapid clearance of recombinant AChEs, allowing long-term circulatory residence of recombinant AChE molecules which are devoid of glycans, or contain glycans devoid of sialic acid capping, or do not assemble into multimeric forms.

It is a further object of the invention to provide pharmaceutically-compatible AChEs from a wide variety of sources, including those which display suboptimal post-translation processing.

It is a further object of the invention to provide a novel use of the modified AChEs of the invention in the prophylactic or acute treatment of OP poisoning.

Other objects and advantages of the invention will become apparent as the description proceeds.

SUMMARY OF THE INVENTION

The present invention relates to a novel class of cholinesterases derivatives wherein the cholinesterase molecules are attached to a water soluble polymer, to a method for preparing such derivatives, and to their uses.

In one aspect the invention is directed to a circulatory long-lived cholinesterases (ChEs) protein, which is a ChEs protein modified with a non-antigenic polymer. According to a preferred embodiment of the invention, the ChE is acetylcholinesterase (AChE). According to another preferred embodiment of the invention, the ChE is butyrylcholinesterase (BChE). As used herein, the term "circulatory long-lived protein" means a protein which, when administered to a subject in vivo, has a mean residence-time in the body of at least several hours, e.g., more than two hours. It should be noted that non-modified recombinant ChEs proteins of the prior art may exhibit very low circulatory mean residence-times, of the order of minutes.

The ChE can be of various origins. For instance, it can be native ChE of mammalian or non-mammalian origin, or recombinant ChE, and it can be further mutated at one or more amino-acid residues.

The non-antigenic polymer is preferably selected from the group consisting of dextran, polyvinyl pyrrolidones, polyacrylamides, polyvinyl alcohols and carbohydrate-based polymers and it preferably comprises a polyalkylene oxide. A preferred polyalkylene oxide is a polyethylene glycol (PEG), such as mono-methoxy-PEG. Furthermore the PEG can be chemically-activated-PEG, such as succinimidyl derivative of PEG propionic acid (SPA-PEG).

The PEG preferred for use in the invention is of molecular weight from about 200 to about 100,000 dalton, preferably from about 2000 to about 40,000 dalton, and more preferably from about 5000 to about 20,000 dalton.

The polymer can be conjugated in different ways, e.g., it can be conjugated through primary amines, carboxyl sites, thiol groups or carbohydrates.

In another aspect, the invention is directed to the use of a physiologically active, long-lived non-antigenic polymer conjugated cholinesterase (ChE) proteins, as an organophosphates scavenger.

The invention further encompasses a pharmaceutical preparation comprising physiologically active, long-lived non-antigenic polymer conjugated cholinesterases (ChEs) proteins, and its use as an organophosphates scavenger.

The invention is also directed to a method for increasing the circulatory half-life of a physiologically active cholinesterase (ChE) protein in vivo, comprising conjugating said ChE with a non-antigenic polymer.

Though cholinesterases from natural sources or from recombinant production systems can potentially serve as bioscavengers of OP compounds, and the invention is by no means limited to the use of ChEs from any specific source, recombinant versions of ChE represent a preferable mode for the formulation of a therapeutical bioscavenger due to the fact that recombinant heterologous production systems enable the introduction of bioscavenging-favorable modifications by site-directed mutagenesis of the ChE genes prior to their introduction into the host cells. Thus, for example, mutations which altered the catalytic performance and which result in the generation of an enzyme form which is less susceptible to irreversible inactivation (aging) can be advantageously used, such as those that were introduced into recombinant ChE, enhancing the bioscavenging potential of the enzymes [Shafferman, A., et al. (1992), J. Biol. Chem. 267, 17640-17648; Shafferman, A., et al. (1993), Proceedings of Medical Defense Bioscience Review, Vol. 3, 1111-1124; Shafferman, A., et al. (1996), Proceedings of Medical Defense Bioscience Review, Vol. 1, 23-32; Ordentlich, A., et al. (1996), Proceedings of Medical Defense Bioscience Review, Vol. 1, 231-239].

DETAILED DESCRIPTION OF THE INVENTION

General Methods and Procedures

1. Cholinesterases

Figure 1:
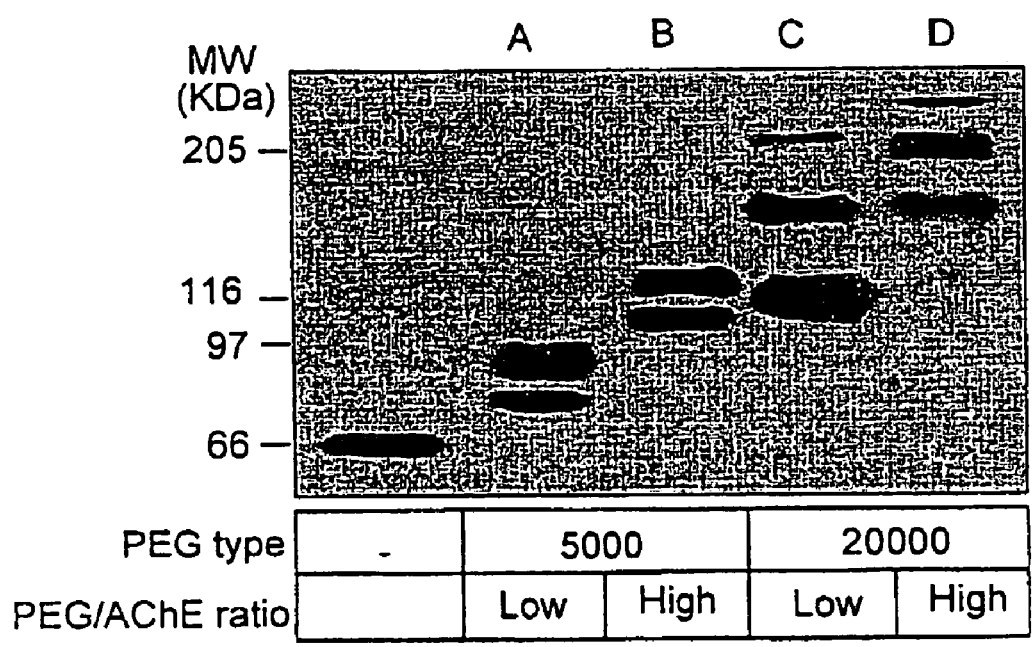
FIG. 1 shows the analysis of PEG-AChE products by SDS-PAGE.

As stated, the present invention is not limited to the use with any particular ChE, and ChEs prepared by various methods can be used. The methods for the preparation of ChEs are well known in the art. For example, AChE or BChE may be prepared by a process comprising the steps of: Extracting from an organ (such as liver, spleen, lung, bone marrow, brain, kidney, placenta and the like), blood cells (such as platelets, white blood cells and the like), plasma, serum and the like, of a mammal (such as rat, bovine, horse, sheep and the like) or non-mammal (such as torpedo, electric eel and the like), and purification thereof, as taught, for instance, in Velan, B., et al. (1991), J. Biol. Chem. 266, 23977-23984, in Kronman, C., et al. (1992), Gene 121, 295-304, or in Lazar, A., et al. (1993), Cytotechnology 13, 115-123.

AChE or BChE may also be prepared by genetic engineering methods, e.g. by inserting a gene encoding AChE or BChE into an appropriate vector, transfecting a host cell by inserting said inserted vector, and purifying the enzyme from the cell extract or from the supernatant fluid of the cultured transfected cells, as discussed in the aforementioned Velan, Kronman and Lazar references. The host cell employed is not limited to any specific cell, and various host cells conventionally used in genetic engineering methods can be used, which are, for example, *Escherichia coli, Bacillus subtilis*, yeast, mold fungi, plant or animal cells and the like. A more specific process for the preparation of AChE or BChE from animal cells comprises the steps of: Transforming an animal cell (such as HEK-293 cells, Chinese Hamster Ovary (CHO) cells, mouse C127 cells, monkey COS cells, Sf (*Spodoptera frugiperda*) cells and the like) with a gene encoding amino acid sequence of AChE or BChE; and purifying the enzyme from the cell extract or from the supernatant fluid of the cultured cells.

AChE or BChE prepared by the above processes include any AChE or BChE that has substantially the same activities such as a partial deletion derivative of the amino acid sequence, a substitution derivative of an amino acid, an insertion derivative of other amino acid sequences, a derivative from binding one or more amino acids to N- or C-terminus of the amino acid sequence, or sugar chain deletion or insertion or substitution derivatives.

2. Polyethylene Glycols

"Polyethylene glycol" or "PEG" refers to mixtures of condensation polymers of ethylene oxide and water, in a branched or straight chain, represented by the general formula H(OCH$_2$ CH$_2$)$_n$OH, wherein n is at least 4. "Polyethylene glycol" or "PEG" is used in combination with a numeric suffix to indicate the approximate average molecular weight thereof. For example, PEG-5,000 refers to polyethylene glycol having a total average molecular weight of about 5,000; PEG-20,000 refers to polyethylene glycol having a total average molecular weight of about 20,000.

To conjugate the ChE to polymers such as poly(alkylene oxides), one of the polymer hydroxyl end-groups is converted into a reactive functional group which allows conjugation. This process is frequently referred to as "activation" and the product is called an "activated" polymer or activated poly (alkylene oxide). Other substantially non-antigenic polymers are similarly "activated" or functionalized. The activated polymers are reacted with AChE or BChE so that attachment occurs at ε-amino groups of lysines, or at the N-terminal amino group. Free carboxylic acid groups, suitably activated carbonyl groups, oxidized carbohydrate moieties and mercapto groups if available on the ChE can also be used as supplemental or alternative attachment sites, if desired. Among the substantially non-antigenic polymers, mono-activated, alkoxy-terminated polyalkylene oxides (PAO's), such as monomethoxy-terminated polyethylene glycols (mPEG's) are preferred.

Suitable polymers will vary substantially by weight. Polymers having molecular number average weights ranging from about 2000 to about 40,000 are usually selected for the purposes of the present invention. Molecular weights of from about 5,000 to about 20,000 are particularly preferred.

As an alternative to PAO-based polymers, effectively non-antigenic materials such as dextran, polyvinyl pyrrolidones, polyacrylamides such as HPMA's-hydroxypropylmethacrylamides, polyvinyl alcohols, carbohydrate-based polymers, copolymers of the foregoing, and the like can be used.

Those of ordinary skill in the art will realize that the foregoing list is merely illustrative and that all polymer materials having the qualities described herein are contemplated as polymers useful in the invention. For purposes of the present invention, "substantially or effectively non-antigenic" means all materials understood in the art as being nontoxic and not eliciting an appreciable immunogenic response in mammals.

General methods of attaching polyethylene glycol to proteins are disclosed, e.g., in U.S. Pat. No. 4,179,337, the description of which is incorporated herein by reference. Other methods of attaching polyethylene glycol are well known in the art, e.g., from U.S. Pat. No. 5,122,614, which is also incorporated herein by reference. Therefore, these methods are not discussed herein in detail, for the sake of brevity.

3. Reaction Conditions

Conjugation reactions, sometimes referred to as PEGylation reactions, are often carried out in solution without regard to where the polymer will attach to the protein. Such techniques are also usually carried out at slightly alkaline pH, i.e. pH 7 to about 9.

The processes of the present invention therefore includes reacting a solution containing AChE or BChE with a suitable amount of a mono-functional methoxy-activated polymer such as succinimidyl derivative of PEG propionic acid (SPA-PEG; Shearwater Polymers, Inc.) at a pH which is sufficient to facilitate covalent attachment of at least a portion of the polymer strands to primary amines, such as the ε-amine of lysine residues or to the N-terminus of the individual AChE or BChE molecules. A preferred (but not limitative) pH is about 8.0.

Conjugation is typically carried out by conducting the attachment reaction with a molar excess of the activated polymer with respect to the primary amines in AChE or BChE. In this regard, the process is typically—but non-limitatively—carried out with about 5 to 400-fold molar excesses, preferably about 20-200-fold molar excesses, and most preferably about 50-100-fold-molar excesses. The conjugation reaction can be conveniently carried out at about room temperature. It is also preferred that the coupling reaction be allowed to proceed for rather short periods of time, i.e. 1-2 hours. In practice, the reaction conditions yield a mixture of polymer-ChE positional isomers. Preferably, each isomer contains several polymer strands attached to the AChE or BChE via an amino acid residue. As will be understood by the skilled person, alternative ChEs (such as BChE) or different AChEs (such as AChE from bovine or other sources or genetically modified version of the enzymes) will provide alternative distributions of positional isomers, depending upon the amino acid sequence of the starting material. Due to the nature of the solution-based conjugation reactions, the compositions are a heterogeneous mixture of species which contains the polymer strand(s) attached at different sites on the ChE molecule. Given that there are multiple possible attachment points for a polymer to an AChE or BChE molecule and given the range of acceptable molar ratios, it will be understood that, in certain embodiments, the conjugate product includes one or more polymeric strands. In such embodiments, the substitutions may range from 1 to about 11 polymers per AChE molecule and from 1 to about 40 polymers per BChE molecule. As will be appreciated by persons skilled in the art, the number of PEG conjugated to ChEs can be controlled in different ways, e.g., by the use of different ChE species, which vary in the number of their lysine residue contents, by the use of mutants in which the number of lysine residues was reduced by site directed mutagenesis, and by the use of other attachment sites such as unique cysteines, as targets for conjugation.

EXAMPLES

All the above and other characteristics and advantages of the invention will be further understood through the following illustrative and non-limitative examples.

Example 1

Preparation of Recombinant Human AChE

A C-terminal truncated version of recombinant human AChE was prepared, to be used for conjugation. Truncation of the C-terminus (a substitution of the last 40 amino acids with a pentapeptide, ASEAP) of the T-subunit of human AChE [Soreq, H., et al. (1990), Proc. Natl. Acad. Sci. USA 87, 9688-9692; accession number for human AChE M55040], was preformed by DNA cassette replacement [Shafferman, A., et al., (1992), J. Biol. Chem. 267, 17640-17648], as described recently [Kryger, G., et al. (2000), Act. Cryst. D56, 1385-1394]. The DNA coding sequences for the truncated HuAChE (ΔC-HuAChE) was inserted into a tripartite expression vector expressing also the reporter gene cat and the selection marker neo [Velan, B., et al. (1991), J. Biol. Chem. 266, 23977-23984; Kronman, C., et al. (1992), Gene 121, 295-304]. Generation of stably transfected HEK-293 cell lines expressing high levels of rHuAChE and purification of the secreted enzyme was performed as described previously [Velan B., ibid; Kronman C., ibid].

Example 2

Attachment of PEG chains to primary amines in rHuAChE was performed using succinimidyl propionate activated methoxy PEG (SPA-PEG; Shearwater polymers, Inc.). Purified ΔC-HuAChE resulting from example 1 (1-5 µM) was incubated with PEG-5000 or PEG-20000 in 50 mM phosphate buffer pH 8.0 for 2 hours at room temperature. PEG was added at a ratio of 5:1(low ratio) or 25:1 (high ratio) [PEG]$_0$/[AChE primary amines]$_0$. The modified products were dialyzed extensively against phosphate buffer saline (PBS). Samples of the proteins were resolved on 7.5% SDS-polyacrylamide gels, electrotransfered onto nitrocellulose and subjected to Western-blot analysis using mouse polyclonal anti-HuAChE antibodies [Shafferman, A. et al., ibid].

The results of the SDS-PAGE analysis are set forth in FIG. 1 which shows the unique migration pattern of discrete bands of the PEG-AChE products generated under the various conditions. It is clear from these results that increasing the PEG to AChE ratio leads to a higher level of lysine occupancy by PEG, and that the use of PEG of higher molecular weight leads to generation of higher molecular weight conjugation products. It should be noted that delicate tuning of conjugation conditions resulted in relatively homogenous products (no more than 2-3 differently PEGylated forms in each preparation).

Example 3

Measurement of the kinetic parameters, as well as inhibition constants of non-modified and PEG-modified AChE demonstrated that, enzymatic performance of AChE was not affected by PEG-conjugation. This is surprising since, for many proteins, PEG conjugation leads to a reduction or loss of their biological activity [Monfardini, C. and Veronese, F. M. (1998), Bioconjug. Chem. 9, 418-450; Francis, G. E., et al. (1998), Inter. J. Hemato. 68, 1-18].

AChE activity was measured according to Ellman et al. [Ellman, G. L., et al. (1961), Biochem. Pharmacol. 7, 88-95]. Assays were performed in the presence of 0.5 mM acetylthiocholine, 50 mM sodium phosphate buffer pH 8.0, 0.1 mg/ml BSA and 0.3 mM 5,5'-dithiobis-(2-nitrobenzoic acid). The assay was carried out at 27° C. and monitored by a Thermomax microplate reader (Molecular Devices). $K_m$ values of HuAChE and PEG-HuAChE for acetylthiocholine were obtained from Lineweaver-Burk plots and $k_{cat}$ calculations were based on active-site titration [Shafferman, A. et al., ibid]. Interactions of HuAChE or PEG-HuAChE with the AChE-specific inhibitors edrophonium, propidium, BW284C51, snake-venom toxin—fasciculin-II and with the organophosphate compound diisopropylfluorophosphate (DFP) were analyzed as described previously [Ordentlich, A., et al. (1996), Proceedings of Medical Defense Bioscience Review, Vol. 1, 231-239]. The comparative results are set forth in the following tables, where Table 1 shows a comparison of catalytic properties of non-modified and PEG-modified ΔC-AChE, and Table 2 is a comparison of inhibition constants of non-modified and PEG-modified C-AChE towards various inhibitors.

TABLE 1

| Kinetic parameters | AChE Preparations | | |
|---|---|---|---|
| | ΔC-AChE | ΔC-AChE-PEG-20000 low ratio | ΔC-AChE-PEG-20000 high ratio |
| $K_m$ (mM) | 0.09 ± 0.01 | 0.09 ± 0.01 | 0.09 ± 0.01 |
| $k_{cat}$ ($10^5 \times min^{-1}$) | 3.9 ± 0.2 | 4.0 ± 0.2 | 3.9 ± .01 |
| $K_{app}$ ($10^8 \times M^{-1} min^{-1}$) | 43 ± 2 | 44 ± 4 | 43 ± 3 |
| $K_{ss}$ (mM) | 9 ± 2 | 6 ± 2 | 10 ± 3 |

*Values are means ± S.D. for at least three independent experiments

TABLE 2

| Inhibitor | AChE Preparations | | |
|---|---|---|---|
| | ΔC-AChE | ΔC-AChE-PEG-20000 low ratio | ΔC-AChE-PEG-20000 high ratio |
| Edrophonium $K_i$ (µM) | 0.8 ± 0.2 | 0.8 ± 0.2 | 0.8 ± 0.2 |
| Propidium $K_i$ (µM) | 1.0 ± 0.3 | 0.6 ± 0.2 | 0.7 ± 0.3 |
| BW284C51 $K_i$ (nM) | 8 ± 1 | 10 ± 2 | 6 ± 1 |
| Fasciculin $K_i$ (nM) | 0.8 ± 0.1 | 0.7 ± 0.2 | 1.1 ± 0.3 |
| DFP $k_i$ ($10^{-4} \times M^{-1} min^{-1}$) | 57 ± 4 | 58 ± 3 | 51 ± 2 |

*Values of inhibition constants are means ± S.D. for at least three independent experiments From the foregoing, it can be seen that the $K_m$ and the $k_{cat}$ values of the modified enzymes were indistinguishable, within the experimental error, from those of the non-modified enzyme (Table 1). Likewise, the inhibition constants ($K_i$) for the classical non-covalent active-site inhibitors or the covalent organophosphate DFP were similar to those of the non-modified AChE (Table 2). Thus it is seen that PEGylation of ΔC-HuAChE can be optimized, to be compatible with maintenance of full enzymatic activity with no apparent effect on reactivity toward various ligands or on the scavenging potential of toxic agents exemplified by the organophosphate diisopropylfluorophosphate (DFP).

Example 4

The pharmacokinetic profiles of non-modified and various preparations of PEG-modified AChE were resolved. Clearance experiments in mice (3 to 6 ICR male mice per enzyme sample) and analysis of pharmacokinetic profiles were carried out as described essentially previously [Kronman, C., et al. (1992), Gene 121, 295-304]. The study was approved by the local ethical committee on animal experiments. Mice were injected with the various rHuAChE preparations (40 µg/mouse in 0.2 ml PBS). Residual AChE activity in blood samples was measured and all values were corrected for background hydrolytic activity in the blood (using samples withdrawn 1 hour before performing the experiment). AChE activity values in samples removed immediately after injection were assigned a value of 100% and used for calculation of residual activity. Background cholinesterase levels in blood of pre-administered mice were less than 2 units/ml. The clearance patterns of the various enzyme preparations were usually biphasic and fitted to a bi-exponential elimination pharmacokinetic model ($C_t=Ae^{-k^\alpha t}+Be^{-k^\beta t}$) as described previously [Kronman, C., et al., 2000, ibid]. This model enables determination of the parameters A and B which represent the fractions of the material removed from the circulation in the first-fast and second-slow elimination phases respectively, and $T_{1/2}\alpha$ and $T_{1/2}\beta$ which represent the circulatory half-life values of the enzyme in the fast and slow phases. The pharmacokinetic parameters MRT (mean residence time, which reflects the average length of time the administered molecules are retained in the organism) and CL (clearance, which represents the proportionality factor relating the rate of substance elimination to its plasma concentration (CL=dose/area under the concentration-time curve), were independently obtained by analyzing the clearance data according to a noncompartmental pharmacokinetic model using the WinNonlin computer program. The comparative results are set forth in Table 3 below.

determining the circulatory time of AChE, is not the number of the modified sites per se, but the actual increase in molecular size as a consequence of the PEGylation. Thus, it appears that the attachment of a single very large PEG unit to HuAChE may be as efficient as PEGylation of all potential lysines by smaller PEG subunits.

Example 5

A circulatory AChE form purified from fetal bovine serum (FBS-AChE) was employed for conjugation. This enzyme form represents, therefore, a native version of AChE, which, by virtue of its serum origin, exhibits a circulation residence ability superior to recombinant forms of the enzyme both human or bovine (see below). FBS-AChE differs from the recombinant human AChE of Example 4, in several respects: (i) the amino acid composition of bovine AChE differs from its human counterpart by 34 amino acids, including 2 lysines (out of 10) that are present in HuAChE but are missing in

TABLE 3

| | Pharmacokinetic parameters | | | | | |
|---|---|---|---|---|---|---|
| ΔC-AChE Preparations | A (% of total) | $T_{1/2}\alpha$ (min) | B (% of total) | $T_{1/2}\beta$ (min) | Clearance (ml/hr/kg) | MRT (min) |
| Non-modified | 74 ± 8 | 3.6 ± 0.6 | 26 ± 2 | 44 ± 3 | 170.4 | 42 ± 3 |
| AChE-PEG-5000 low ratio | 56 ± 9 | 29 ± 6 | 43 ± 3 | 390 ± 50 | 14.2 | 510 ± 70 |
| AChE-PEG-5000 high ratio | 46 ± 3 | 28 ± 5 | 64 ± 3 | 540 ± 70 | 13.2 | 740 ± 80 |
| AChE-PEG-20000 low ratio | 35 ± 3 | 32 ± 5 | 65 ± 5 | 750 ± 130 | 12 | 950 ± 120 |
| AChE-PEG-20000 high ratio | 23 ± 4 | 35 ± 15 | 76 ± 3 | 1550 ± 120 | 4.3 | 2100 ± 200 |

Figure 2:
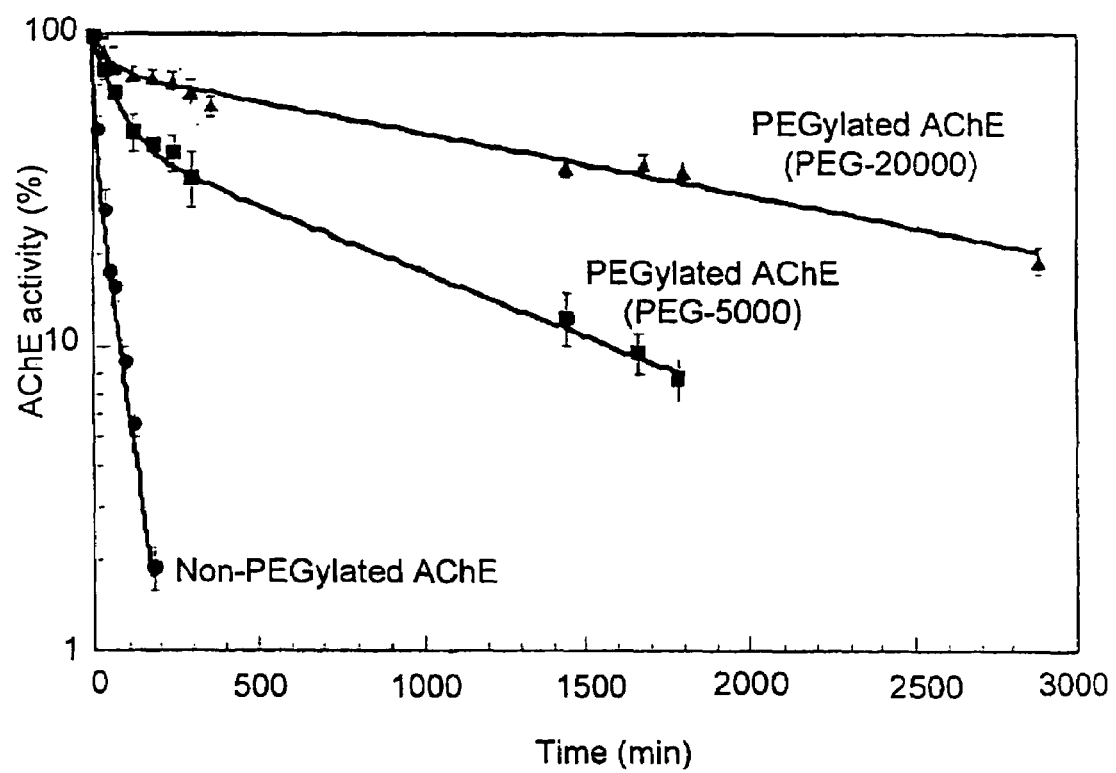
FIG. 2 shows the pharmacokinetic profiles of non-modified and PEG-modified AChE.

The pharmacokinetic characteristics of the different PEG-AChE preparations are also set forth in FIG. 2 which shows pharmacokinetic profiles of non-modified and PEG-modified AChE.

As it is seen from the results reported above, in all cases circulatory residence is significantly improved by PEG conjugation. The most prominent effect was observed following modification of ΔC-HuAChE with either PEG-5000 or PEG-20000 at the higher PEG to AChE ratio. In the latter case, the MRT was 50 times longer than that of the non-modified enzyme. Such a high MRT value in ICR mice, exceeds by far most of the previously reported values for different types of AChE or BChE molecules from either recombinant, native or serum derived origin [Kronman, C., et al. (1995) Biochem. J. 311, 959-967; Saxena, A., et al. (1997) Biochem. 36, 7481-7489].

Figure 3:
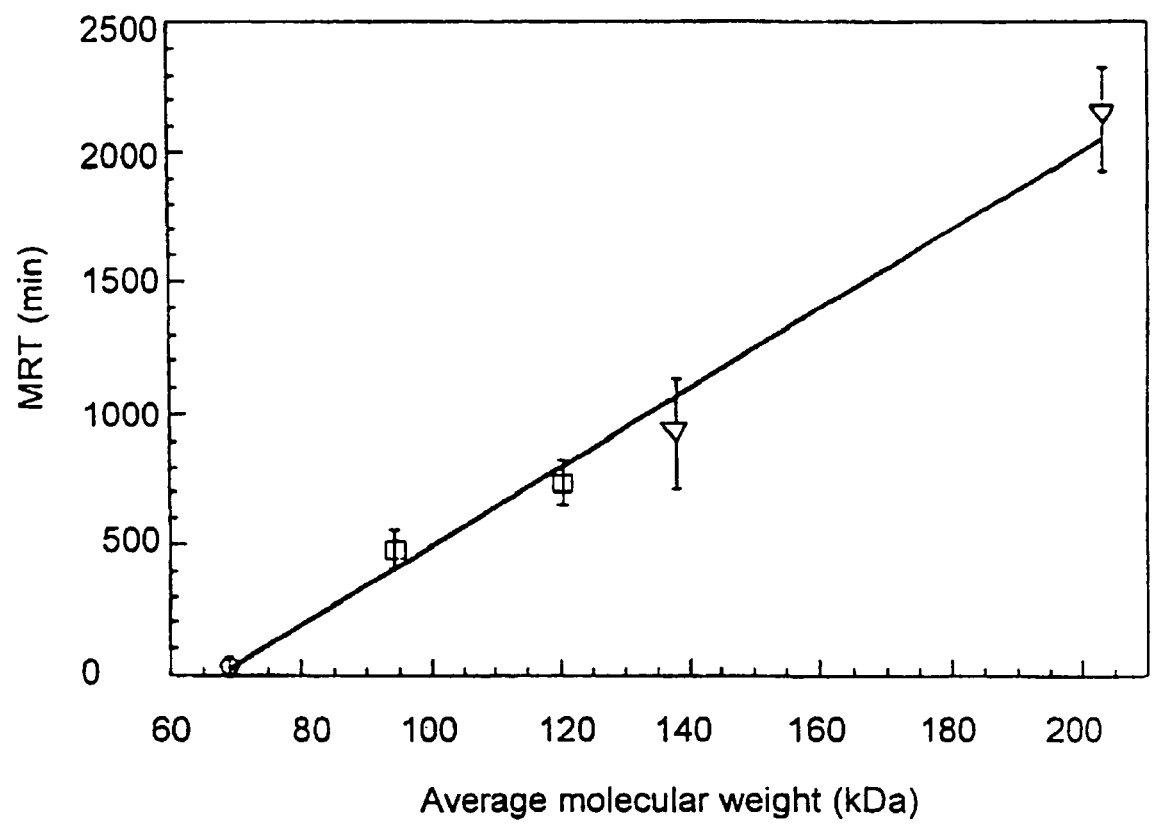
FIG. 3 shows the correlation of MRT and the molecular weight of the conjugated proteins.
Figure 4:
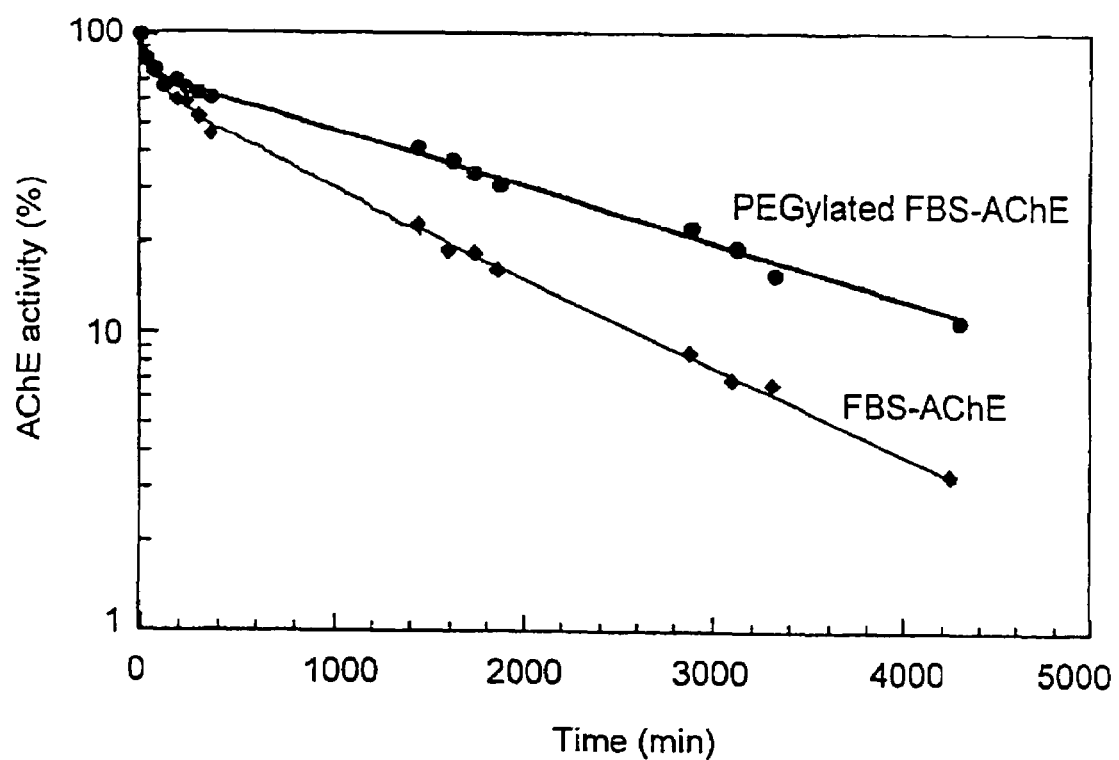
FIG. 4 shows the pharmacokinetic profiles of non-PEGylated and PEGylated FBS-AChE.
Figures 5A, 5B:
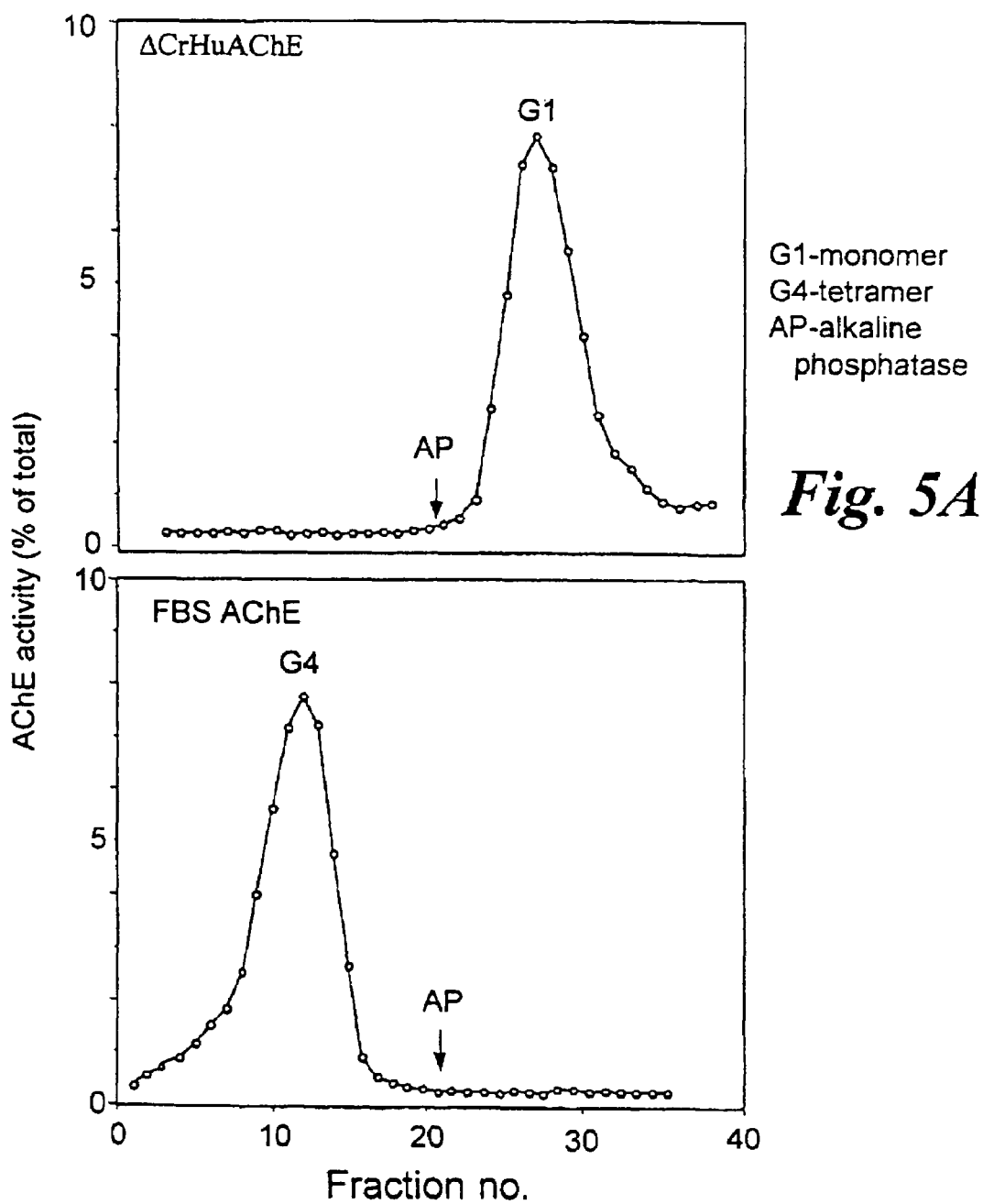
FIG. 5 Shows the sucrose gradient sedimentation profiles of ΔC-rHuAChE and FBS-AChE.

The MRT values of the various PEG-modified AChE preparations (differing in the number and size of the appended PEG molecules), as presented in Table 3, is linearly dependent on the overall apparent molecular weight of the PEGylated-HuAChE preparation (the "average" apparent molecular weight for each of the preparations was computed by determination of the relative abundance of PEGylated products in a given preparation by subjecting its SDS-PAGE Western blots profile to densitometric analysis). The finding of the linear relationship in FIG. 3 suggests that the factor BoAChE [Mendelson, I., et al. (1998) Biochem. J. 334, 251-259], (ii) the bovine version of the enzyme contains four sites of N-glycosylation rather than three exhibited by the human form [Mendelson, I., et al., 1998, ibid], (iii) the native FBS-AChE displays fully sialylated glycan termini (Kronman, C., et al., 2000, ibid), (iv) as is set forth in FIG. 5, FBS-AChE is tetrameric in nature whereas the C-terminal truncated version of AChE (Example 4) is monomeric (analytical sucrose density gradient centrifugation was performed as described [Kronman, et al., 1995, ibid]) and (v) FBS-AChE displays a MRT of 1340 min (compare to the truncated rHuAChE from Example 4 which exhibits, in its non-PEGylated state, a MRT of 42 min). FBS-AChE was purified from serum as described in Example 1. The purified enzyme was conjugated to SPA-PEG as described in Example 2. Clearance experiments in mice and analysis of pharmacokinetic profiles were carried out as described in Example 4. The comparative pharmacokinetic profiles of non-modified and PEG modified FBS-AChE are set forth in FIG. 4. From the foregoing it is clearly seen that modification of FBS-AChE by PEG significantly improved its pharmacokinetic behavior. Moreover, together with Example 4, it is clear that the improvement of circulatory longevity by PEG modification is not dependent on the origin of the enzyme (e.g. recombinant or native; human or bovine). The findings that modification of both forms by PEG resulted in a long lived enzyme (Example 4 and this example), indicates that conjugation of PEG increases circulatory retention regardless of amino-acid sequence divergence, number of appended glycans, level of N-glycan terminal sialylation and oligomeric nature of the enzyme.

Example 6

Figure 6A:
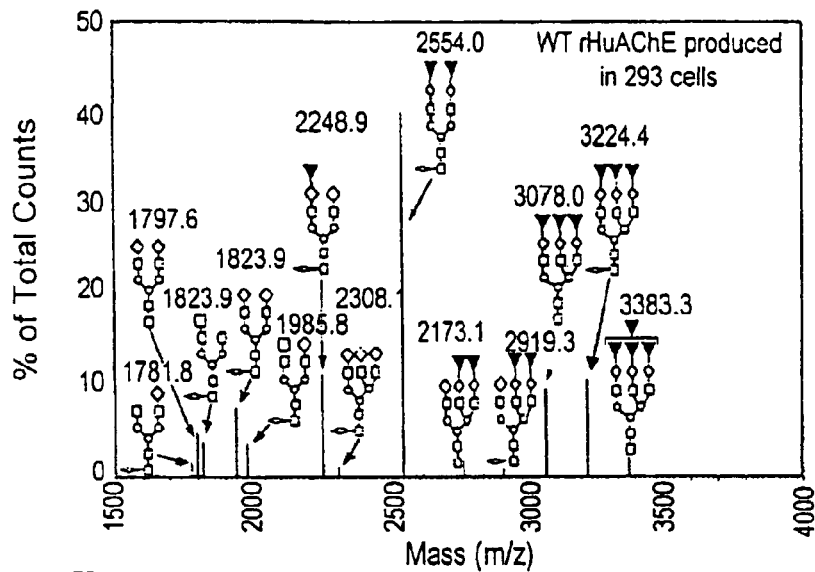
FIG. 6 shows the glycan analysis of the desialylated, oversialylated and native recombinant human AChE.
Figure 6B:
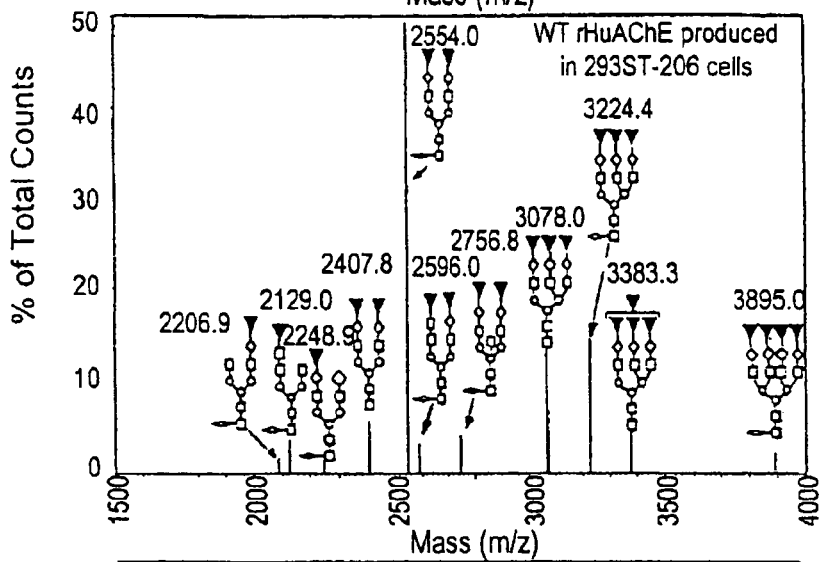
Figure 6C:
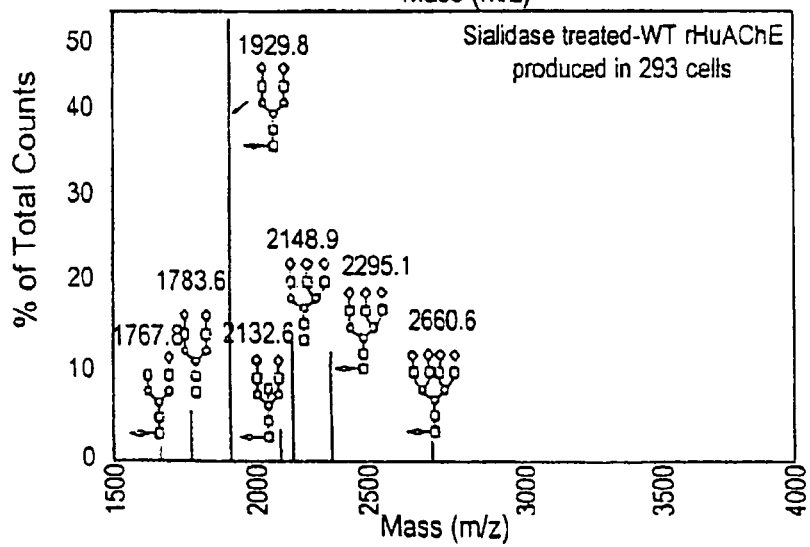
Figure 7:
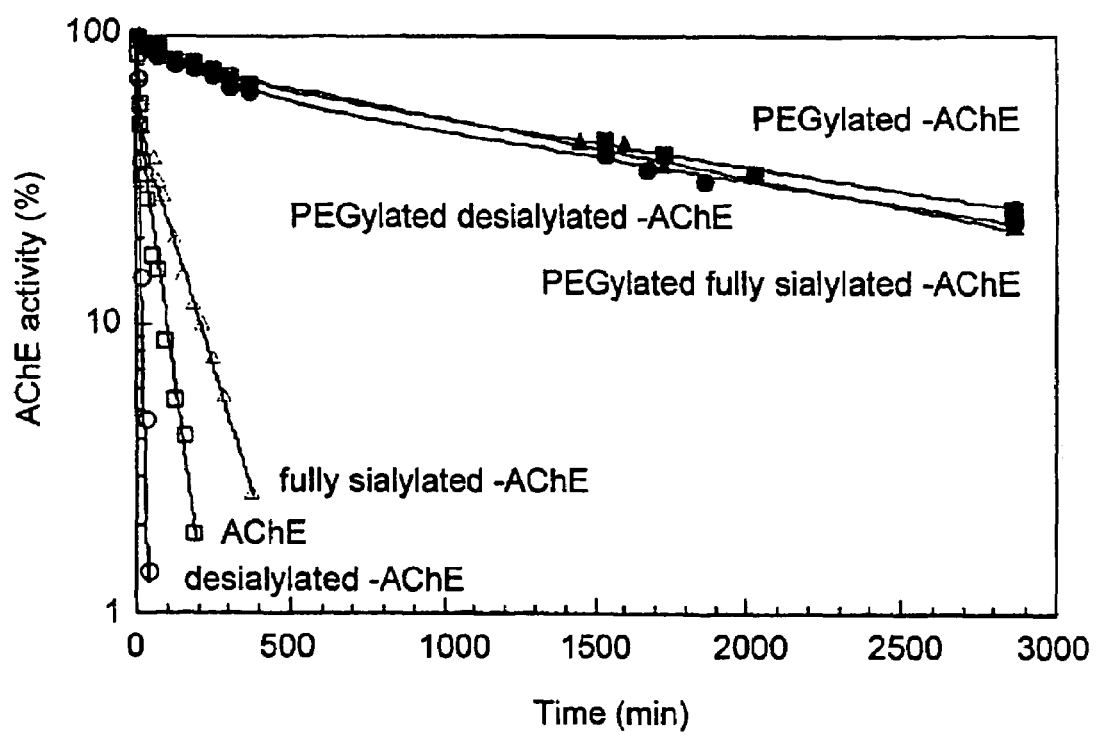
FIG. 7 shows the pharmacokinetic profiles of non-PEGylated and PEGylated desialylated-AChE, over-sialylated-AChE and native AChE.

The pharmacokinetic improvement of AChE promoted by PEG-conjugation was studied in conjunction with the terminal sialylation level of the N-glycans appended to the enzymes. The way sialylation and PEG-modification may interplay in determining serum residence time of AChE is of special importance due to the crucial role of efficient sialylation in preserving circulatory longevity of AChE (Kronman, C., et al., 1995, ibid; Chitlaru, T., et al., 1998, ibid; Kronman, C., et al., 2000, ibid), probably involving the hepatic asialoglycoprotein receptor which efficiently mediates rapid clearance of undersialylated (bearing exposed gal residues) glycoproteins [Ashwell, G. and Harford, J. (1982), Ann. Rev. Biochem. 51:531-554]. Notably, in many recombinant systems high level of heterologous glycoprotein production is associated with low level of sialic acid capping. Indeed, it has been documented that a direct correlation exists between the level of AChE production and the extent of N-glycan terminal sialylation, resulting in severe undersialylation and hence, poor pharmacokinetic performance of rHuAChE generated by high producer clones [Chitlaru, T., et al., 1998, ibid]. In this example therefore, non-sialylated or fully-sialylated AChE forms were used for PEG conjugation. Recombinant AChE was purified from tissue culture medium as described in Example 1. Generation of desialylated rHuAChE was achieved by subjecting the purified enzyme to treatment with sialidase (neuroaminidase) as described before [Chitlaru, T., et al., 1998, ibid]. Generation of fully sialylated rHuAChE was achieved by expressing the HuAChE gene in the genetically modified 293ST-2D6 cells which stably express a recombinant rat Golgi-version of 2,6 sialyltransferase [Chitlaru et al., 1998, ibid, Kronman et al., 2000, ibid]. The fully sialylated AChE was purified from tissue culture medium as described in Example 1. The sialidase-treated or the fully sialylated enzymes were conjugated to PEG as described in Example 2. Glycan structures of these AChEs were determined by MALDI-TOF analysis as described in the art [Kronman, C., et al., 2000, ibid]. Analysis of glycan structures and level of sialylation is set forth in FIG. 6. Clearance experiments in mice and analysis of pharmacokinetic profiles were carried out as described in Example 4. The comparative pharmacokinetic profiles are set forth in FIG. 7. From the foregoing it is clearly seen that modification of the sialidase-treated or fully sialylated AChE by PEG significantly improved their pharmacokinetic behavior. Moreover, it is clear that the improvement of circulatory longevity by PEG modification is not dependent on the nature of the appended glycans of the enzyme, and that PEG conjugation can rescue an extremely circulatory short lived form of the enzyme, as well as compensate for low level of sialic acid occupancy which is pharmacokinetically deleterious.

Example 7

Figure 8:
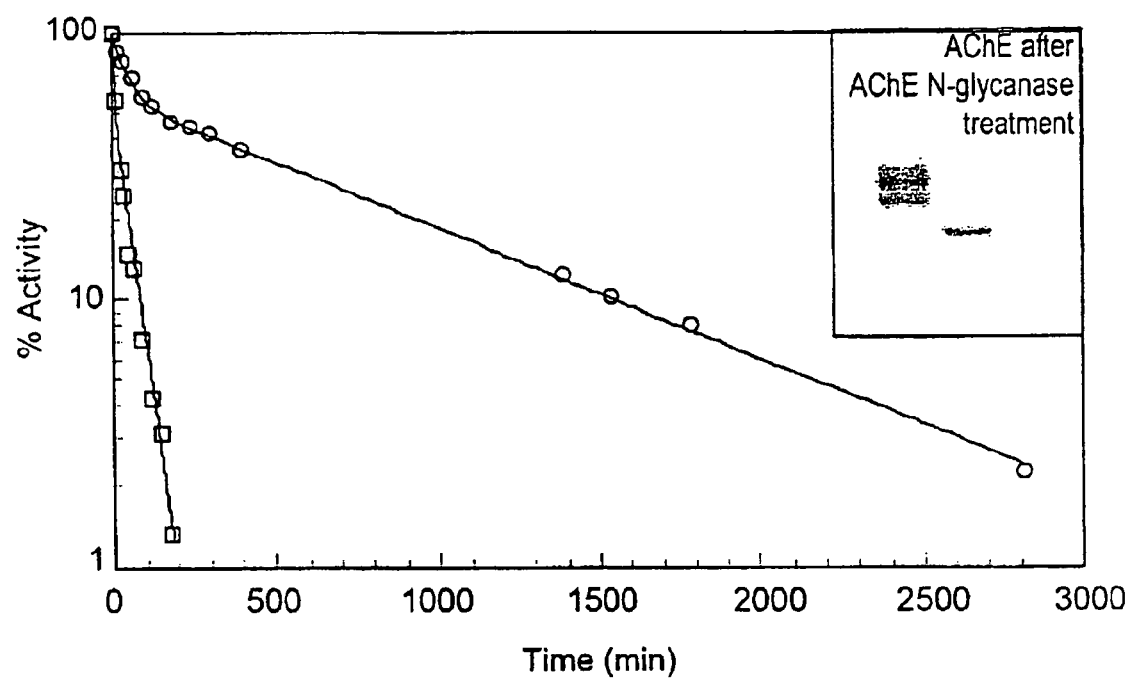
FIG. 8 shows the pharmacokinetic profiles of non-PEGylated and PEGylated deglycosylated-AChE.
Figure 10:
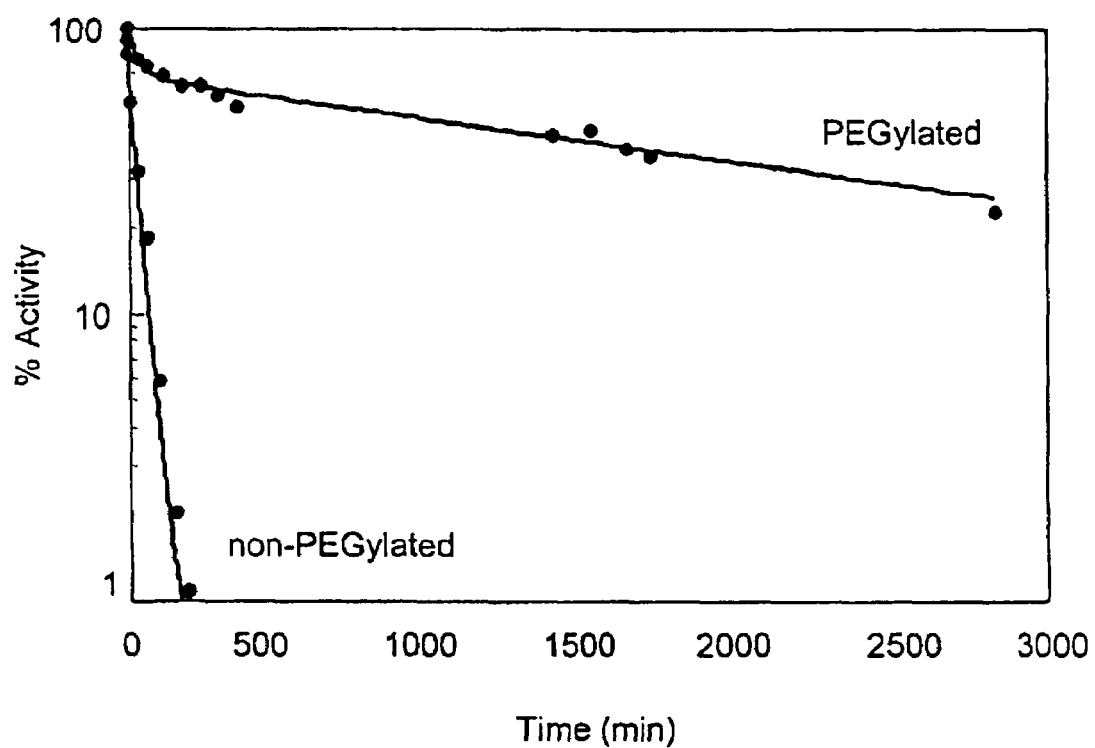
FIG. 10 shows the pharmacokinetic profiles of non-PEGylated and PEGylated N350Q/N464Q-AchE.

Recombinant human AChE which carries one, instead of three appended glycans, or which is completely non-glycosylated, was used for conjugation. The ability of PEG to promote pharmacokinetic improvement of AChE with a reduced number of appended N-glycans is of special interest in view of the fact that recombinant proteins generated in bacterial systems do not contain glycans. To examine the effect of PEG-conjugation on AChE carrying a reduced number of N-glycan appendages, a mutated recombinant human AChE (N350Q/N464Q) which results in the generation of AChEs harboring one glycan per molecule was used for conjugation. The recombinant AChE was purified from tissue culture medium as described in Example 1. To generate AChE which is completely devoid of N-glycans, recombinant AChE was generated and purified from tissue culture medium as described in Example 1. The purified enzyme was treated with N-glycanase to remove all N-linked glycan structures. Recombinant AChE (250-500 µg of either the wild-type or the C-terminal truncated enzyme) was subjected to treatment with 250 mU of N-glycanase (Glyko Inc. or Boehringer Manheim GmbH) at room temperature for 48 hours. N-glycanase was removed by subjecting the treated enzyme to a second round of purification as described in Example 1. The complete removal of the glycans from AChE was monitored by SDS-PAGE analysis and is set forth in the inset of FIG. 8. The monoglycosylated AChE and the non-glycosylated enzyme were conjugated to PEG as described in Example 2. Clearance experiments in mice and analysis of pharmacokinetic profiles were carried out as described in Example 4. The comparative pharmacokinetic profiles of non-modified and PEG-modified non-glycosylated AChE are set forth in FIG. 8. The comparative pharmacokinetic profiles of non-modified and PEG-modified mono-glycosylated AChE are set forth in FIG. 10. From the foregoing it is clearly seen that modification of the monoglycosylated or non-glycosylated AChE by PEG significantly improved their pharmacokinetic behavior. These results show that the improvement of circulatory longevity by PEG modification is not dependent on the presence or the quantity of appended glycans of the enzyme.

Example 8

Figure 9A:
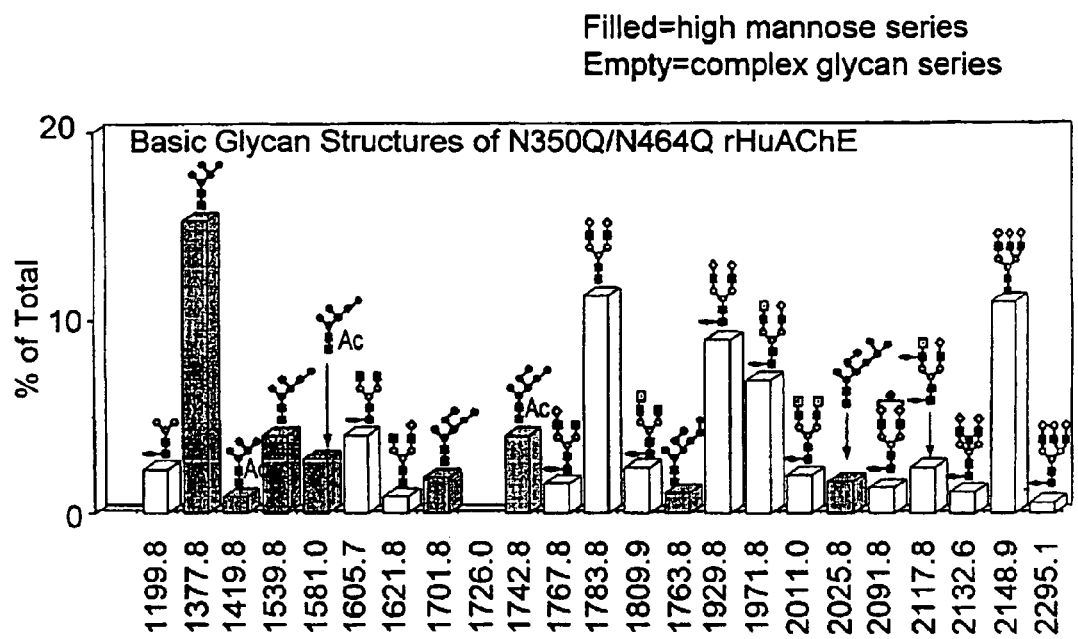
FIG. 9 shows the glycan analysis of WT and N350Q/N464Q mutated recombinant human AChE.
Figure 9B:
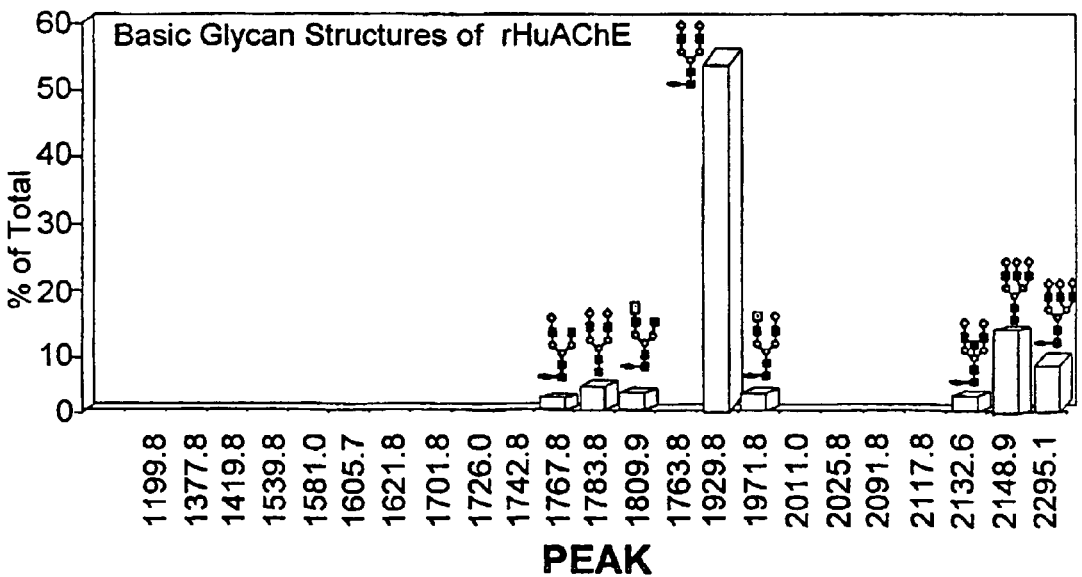

A mutated recombinant human AChE (N350Q/N464Q) was used for conjugation. Notably, the mutations N350Q and N464Q of this form of enzyme result in the generation of AChEs harboring one glycan per molecule. The recombinant AChE was purified from tissue culture medium as described in Example 1. The glycan structures of this mutant were determined by MALDI-TOF analysis as known in the art [Kronman, C., et al., 2000, ibid]. The glycan analysis is set forth in FIG. 9. The glycan analysis revealed that approximately 50% of the glycans appended to this mutant form of AChE are of the high-mannose type. In addition to the high mannose type of N-glycans associated with this form of enzyme, the MALDI-TOF analysis revealed the presence of a substantial fraction of molecules harboring immature glycans (terminating in GalNAc, see FIG. 10). The purified enzyme was conjugated to PEG as described in Example 2. Clearance experiments in mice and analysis of pharmacokinetic profiles were carried out as described in Example 4. The comparative pharmacokinetic profiles are set forth in FIG. 10. From the foregoing it is clearly seen that modification of this mutant AChE by PEG significantly improved its pharmacokinetic behavior.

Example 9

Figure 11:
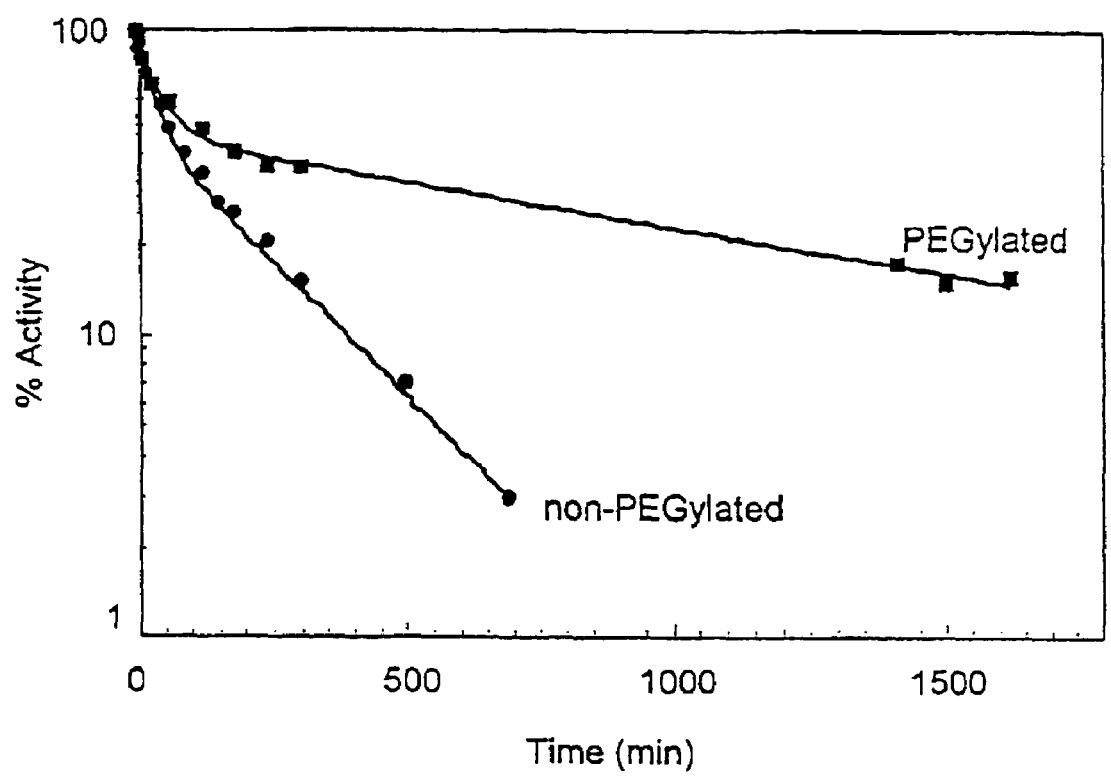
FIG. 11 shows the pharmacokinetic profiles of non-PEGylated and PEGylated BChE (partially sialylated).

Equine BChE (accession number AAF61480) was subjected to lysine-directed modification by PEG, followed by assessment of its pharmacokinetic behavior. Equine BChE was purified from horse serum by affinity to procainamide as described in Example 1. BChE was partially desialylated by enzymatic treatment with neuraminidase as described in Example 6, subjected to PEG conjugation as described in Example 2 and administered to mice for pharmacokinetic characterization as described in Example 4. Unlike the non-treated serum-derived BChE which resides in the circulation for extended periods of time, the partially desialylated enzyme displays a dramatically shortened circulatory residence time (MRT=160 min, see FIG. 11). However, when this sub-optimally sialylated enzyme was subjected to PEG attachment, the circulatory residence time was significantly increased, to levels commensurate with those exhibited by the native, long-lived enzyme.

Although belonging to the same family of cholinesterases as AChE, BChE differs from human AChE by more than 330 amino acids. Most notably, the equine version of BChE contains 33 lysine residues and 9 glycans per enzyme subunit as opposed to 7 lysine residues and 3 glycans present in the truncated version human AChE. The ability to extend the circulatory residence of equine butyrylcholinesterase illustrates the feasibility of PEG-modification procedure to generate long-lived OP-bioscavengers from a wide variety of cholinesterases differing in their source, primary sequence, lysine and glycan contents and enzymatic specificities.

We claim:

1. A soluble, circulatory long-lived organophosphate scavenger with a mean residence-time (MRT) in the body of at least 500 minutes, which scavenger is a recombinant cholinesterase (ChE) protein conjugated to polyethylene glycol (PEG); said ChE being selected from acetylcholinesterase (AChE) and butyrylcholinesterase (BChE), and said PEG having molecular weight of from about 5000 to about 20,000 dalton; wherein the number of PEG molecules conjugated to one ChE molecule ranges from 1 to 11 for said AChE, and from 1 to 40 for said BChE.

2. The scavenger of claim 1 wherein the recombinant AChE is mutated at one or more amino-acid residues.

3. The scavenger of claim 1 lwherein the recombinant BChE is mutated at one or more amino-acid residues.

4. The scavenger of claim 1 wherein the polyethylene glycol is mono-methoxy-PEG.

5. The scavenger of claim 4 wherein the PEG is chemically-activated-PEG.

6. The scavenger of claim 5 wherein the chemically-activated-PEG is succinimidyl derivative of PEG propionic acid (SPA-PEG).

7. The scavenger of claim 1 wherein the PEG is conjugated through primary amines, carboxyl sites, or thiol groups, or carbohydrates.

8. A pharmaceutical preparation comprising the scavenger of claim 1.

* * * * *

UNITED STATES PATENT AND TRADEMARK OFFICE
CERTIFICATE OF CORRECTION

PATENT NO.       : 7,572,764 B2  
APPLICATION NO.  : 10/476338  
DATED            : August 11, 2009  
INVENTOR(S)      : Cohen et al.

Page 1 of 1

It is certified that error appears in the above-identified patent and that said Letters Patent is hereby corrected as shown below:

Title page, item [54] title should read as follows: "Uses of chemically-modified cholinesterases for detoxification of organophosphorus compounds"

Signed and Sealed this

Twenty-ninth Day of September, 2009

David J. Kappos  
*Director of the United States Patent and Trademark Office*

UNITED STATES PATENT AND TRADEMARK OFFICE
CERTIFICATE OF CORRECTION

PATENT NO. : 7,572,764 B2  Page 1 of 1
APPLICATION NO. : 10/476338
DATED : August 11, 2009
INVENTOR(S) : Cohen et al.

It is certified that error appears in the above-identified patent and that said Letters Patent is hereby corrected as shown below:

Title page, item [73] Assignee's city should read -- Nes Ziona --

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,572,764 B2 | Page 1 of 1 |
| APPLICATION NO. | : 10/476338 | |
| DATED | : August 11, 2009 | |
| INVENTOR(S) | : Cohen et al. | |

It is certified that error appears in the above-identified patent and that said Letters Patent is hereby corrected as shown below:

Title page, item [54] and Column 1, lines 1-3, title should read as follows: "Uses of chemically-modified cholinesterases for detoxification of organophosphorous compounds"

This certificate supersedes the Certificate of Correction issued September 29, 2009.

Signed and Sealed this

Tenth Day of November, 2009

David J. Kappos
*Director of the United States Patent and Trademark Office*